United States Patent [19]

Gross

[11] B  4,056,502

[45]  Nov. 1, 1977

[54] ABSORBENT ARTICLES MADE FROM CARBOXYLIC POLYELECTROLYTE SOLUTIONS CONTAINING BIS-OXAZOLINE CROSSLINKER AND METHODS FOR THEIR PREPARATION

[75] Inventor: James R. Gross, Lake Jackson, Tex.

[73] Assignee: The Dow Chemical Company, Midland, Mich.

[21] Appl. No.: 494,440

[22] Filed: Aug. 5, 1974

[44] Published under the second Trial Voluntary Protest Program on February 17, 1976 as document No. B 494,440.

[51] Int. Cl.² .............................................. C08F 20/06
[52] U.S. Cl. ..................... 260/29.6 N; 260/29.6 TA; 260/33.4 R; 260/29.6 HN; 260/79.3 R; 260/79.5 P; 260/79.3 M; 260/80 P; 526/14; 526/51; 526/240; 526/258; 526/260; 526/319; 128/156; 428/255; 428/264
[58] Field of Search ....... 260/29.6 N, 80.73, 29.6 TA, 260/29.6 HN, 29.6 SQ, 29.6 E, 79.3 R, 86.1 R, 86.1 N, 88.1 R, 80 P, 88.1 PC, 79.3 M, 80.3 E, 85.7

[56]  References Cited

U.S. PATENT DOCUMENTS

| 3,669,103 | 6/1972 | Harper et al. | 128/156 |
| 3,755,237 | 8/1973 | Isaacs | 260/29.6 TA |
| 3,812,070 | 5/1974 | Kelley | 260/29.6 TA |

FOREIGN PATENT DOCUMENTS 2,012,809  10/1971  Germany.

*Primary Examiner*—Harry Wong, Jr.
*Assistant Examiner*—Peter F. Kulkosky
*Attorney, Agent, or Firm*—Benjamin G. Colley;

[57]  ABSTRACT

Water swellable absorbent articles, made from polyelectrolytes, containing free carboxylic groups, together with methods for their preparation, and a composition useful to make said articles are disclosed. The composition contains bis-oxazolines or bis imino oxazolidines. The articles are crosslinked by heating and/or removing substantially all of the water from the precursor composition.

The absorbent articles are useful as surgical sponges, diapers, tampons, meat trays, bath mats and the like.

13 Claims, No Drawings

ABSORBENT ARTICLES MADE FROM CARBOXYLIC POLYELECTROLYTE SOLUTIONS CONTAINING BIS-OXAZOLINE CROSSLINKER AND METHODS FOR THEIR PREPARATION

BACKGROUND OF THE INVENTION

This invention relates to water swellable absorbent articles made from crosslinked polyelectrolytes, methods for their preparation, and to an aqueous solution consisting of polyelectrolytes containing free carboxylic groups which is useful to make absorbent articles.

It is known from U.S. Pat. Nos. 3,669,103 and 3,670,731 that cross-linked polymeric sorbents can be sandwiched between flexible supports to achieve disposable diapers or dressings.

It is further known from U.S. Pat. Nos. 2,988,539; 3,393,168; 3,514,419 and 3,557,067 that water swellable cross-linked carboxylic copolymers can be prepared. However, these prior art copolymers are all crosslinked during copolymerization or crosslinked after polymerization with subsequent neutralization of the carboxylic acid groups to form water swellable polyelectrolytes and hence these prior art polyelectrolytes cannot be crosslinked in situ as a coating on a substrate or as a flexible film thereof.

It is further known from Ser. No. 468,794, filed May 9, 1974 that carboxylic synthetic polyelectrolytes can be crosslinked after polymerization by the use of a nucleophilic displacement reaction using polyhaloalkanols, sulfonium zwitterions, haloepoxy alkanes, polyglycidyl ethers and mixtures thereof. These crosslinkers are active over a pH range from acidic to basic and must therefore be shipped separately and added to the polyelectrolyte solution at the point of use rather than the point of manufacture. The advantage of the present invention is that the crosslinking reaction proceeds only under acidic conditions and the user need only acidify the pre-mixed polyelectrolyte and crosslinker to achieve a crosslinkable composition useful in fabricating absorbent articles. The acidification is much less critical than adding the exact amount of crosslinker so the chance of error spoiling a batch is minimized for the user.

SUMMARY OF THE INVENTION

The present invention comprises a composition having a pH in the range from 1.0 to 6.5 and preferably in the range from 4.0 to 6.0 which is useful to form water swellable articles of a carboxylic type synthetic polyelectrolyte which consists of a solvent such as lower alcohols, water, or mixtures thereof, about 5 to about 60 percent, preferably about 15 to about 40 percent by weight, based on the solvent, of a carboxylic polyelectrolyte, and 0.05 to 5.0% by weight and preferably 0.2 to 0.5% by weight, based on the polyelectrolyte, of a oxazolo type crosslinking agent reactive with free carboxylic groups. The crosslinking agent can be selected from classes such as 2-oxazolines and 2-imino-oxazolidines and mixtures thereof.

The invention further comprises methods of making discrete films, absorbent articles, particulates, fibers, and the products of these processes wherein the above solution on various substrates, is heated to a temperature greater than about 30°C and preferably from about 90° to about 150°C. to effect the crosslinking of the polyelectrolyte and to remove excess solvent.

In order to obtain very high production rates of absorbent articles, it may be desirable to replace part or nearly all of the water in the polyelectrolyte solution with a lower alcohol such as methanol or ethanol. This substitution results in lower solution viscosities at a given percent solids and promotes rapid drying.

The final products of the present invention are thus water swellable and are useful where ever aqueous solutions need to be absorbed. Examples of the diverse utilities are surgical sponges, catemenial tampons, diapers, meat trays, paper towels, disposable door mats, disposable bath mats and disposable litter mats for household pets.

DETAILED DESCRIPTION

Examples of carboxylic synthetic polyelectrolytes useful in this invention are the ammonium or alkali metal salts of homopolymers of acrylic or methacrylic acid and copolymers with one or more ethylenically unsaturated comonomers. The only limitation being that any copolymer, to be useful in preparing highly absorbent polymer according to this invention, must be essentially water soluble in the salt form and must contain a minimum of 2 mole percent of an olefinically unsaturated carboxylic acid polymerized therein. The alternating copolymers of maleic anhydride and the maleic and fumaric acids and esters are useful when rendered water soluble by an appropriate base. One skilled in the art of radical addition copolymerization could prepare any number of suitable heteropolymers containing sufficient carboxylic functionality to render them water soluble and thus be useful in this invention.

The following list of polymers is representative of those which can be prepared from readily available monomers and converted to useful polyelectrolytes:

acrylic acid - acrylate copolymers
acrylic acid - acrylamide copolymers
acrylic acid - olefin copolymers
polyacrylic acid
acrylic acid - vinyl aromatic copolymers
acrylic acid - styrene sulfonic acid copolymers
acrylic acid - vinyl ether copolymers
acrylic acid - vinyl acetate copolymers
acrylic acid - vinyl alcohol copolymers
copolymers of methacrylic acid with all the above comonomers
copolymers of maleic acid, fumaric acid and their esters with all the above comonomers
copolymers of maleic anhydride with all the above comonomers If desired, the foregoing polyelectrolytes can also be sulfonated by treatment with $SO_3$, chlorosulfonic acid or fuming sulfuric acid in an inert organic solvent.

Illustrative examples of the soluble crosslinking agents useful in this invention are compounds having the following formulae I. 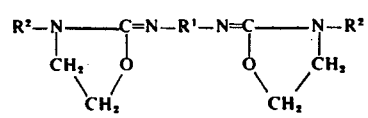

II. 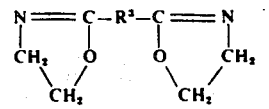

wherein $R_1$ is a divalent radical such as alkylidenes, arylidenes, cyclomethylidenes and the like, $R_2$ is a monovalent hydrocarbon radical such as an alkyl group of one to ten carbons, cyclohexyl and phenyl, $R_3$ is a single bond; a divalent alkylene ether group such as oxydiethylene and oxydibutylene; a divalent alkylene thioether group such as thiodiethylene and thiodibutylene; and a divalent alkylidene group such as ethylene, tetramethylene.

Specific examples of $R_1$ alkylidene groups are methylene, ethylene, trimethylene, and tetramethylene groups. Examples of $R_1$ arylidene groups are m-phenylene, p-phenylene, 4,4'-bisphenylene, 3,3'-biphenylene, methylene diphenyl, etc.

Examples of $R_1$ cyclomethylidene groups are cyclohexylene, methylene dicyclohexylene, and the like.

Specific useful compounds falling within the above formulae are
phenylene bis(imino-N-phenyl oxazolidine)
methylene bis(phenylimino-N-phenyl oxazolidine)
oxydiethylene-2,2'-bis(2-oxazoline)
thiodiethylene-2,2'-bis(2-oxazoline)
2,2'-bis(2-oxazoline)
tetramethylene-1,4-bis(2-oxazoline)
Other useful compounds are disclosed in U.S. Pat. No. 3,758,629.

The crosslinking technique used in this invention to transform water soluble polyelectrolytes into insoluble but water swellable polymers can be called a ring-opening cure.

The rate of ring opening is concentration dependent and is a factor in this invention. In solution, when the concentration of the cross-linker is very low, the rate of reaction is quite slow (pot life 10–48 hours before gelation). Once the solution is applied to a substrate surface and evaporation of solvent begins, the rate of cross-linking accelerates. Applying heat at this time increases the reaction rate even more.

If the cross-linking reaction is allowed to proceed in the original solution as by heating, aging, or excessive amounts of cross-linker, the absorbent articles of this invention cannot be fabricated. The solution will become progressively more viscous and stringy until it forms a continuous gel which could not be spread, sprayed or spun.

In the method of making water swellable films by the present invention the above solution of the polyelectrolytes is spread on a flat plate or roller of metal, plastic, or other impervious substrate and heated to a temperature greater than 30°C. to crosslink the polyelectrolyte and drive off the excess water and/or alcohol. The film is then peeled off the plate or roller by a scraper to recover the intact film for subsequent storage or use.

It is sometimes desirable to add a small amount of a surfactant to the polyelectrolyte solution to aid in flowing on and removing the continuous film from the water impervious substrate. A secondary benefit of using a surfactant is to increase the wettability of the final dry absorbent film. Either anionic or nonionic surfactants may be used. Examples of the useful surfactants are the sodium alkyl sulfonates and ethylene oxide derivatives of alkylated phenols and the like.

Similarly, when an absorbent article is prepared, the article which is to be the substrate is coated with the solution of the polyelectrolyte and then the coating is crosslinked. It is to be understood that for the purposes of this invention the coating step implies a complete coating or a discontinuous coating. Thus when a fiberous substrate such as cellulose batting, paper, woven or non-woven cloth, and the like are used as the substrate, the solution can be applied in a discontinuous manner, i.e., in a pattern of large dots, squares, or grid lines to retain the inherent flexibility of the fiberous substrate and at the same time vastly improve its water absorbency. In this instance plasticizers are not needed. Wood pulp can be coated by slurrying it in the polyelectrolyte solution followed by a fluffing operation.

If desired, the water swellable film prepared as above can be used per se as the inner absorbent layer in baby diapers. It is sometimes advantageous that the film be disintegrated into flakes, strips, or powders. This is accomplished by crushing or comminuting the film in a hammer mill, blenders, or the like. If long flat strips are desired, the film can be sliced widthwise with appropriate slicers.

In some instances, water swellable fibers are desired. These can be prepared by extruding the above solution of the polyelectrolytes into a bath comprising lower alkyl ketones such as acetone, methyl ethyl ketone, diethyl ketone and the like. Alcoholic solutions may be extruded into a non-aqueous coagulant such as chlorinated hydrocarbons, i.e., methylene chloride, perchloroethylene and the like. The soft extruded fibers are then removed from the bath by any convenient means such as a three or five roll cluster and carried through a heated chamber at a temperature greater than about 30°C. and preferably in the range from about 70° to about 150°C. to dry and to crosslink the polyelectrolyte fibers.

The absorbency of the crosslinked polyelectrolytes (grams solution gelled per gram of polyelectrolyte) is determined in the following manner using synthetic urine (0.27 N sodium chloride solution).

A 0.5 gram sample of a crosslinked polyelectrolyte is weighed into a 250 ml. beaker, a 0.27 N sodium chloride solution (150 ml.) is poured into the beaker and allowed to soak for 2 hours at room temperature, with occasional stirring. The swelled polyelectrolyte is then collected by filtration and the gel capacity is reported as grams of solution gelled per gram of polymer salt.

The following examples are presented solely to illustrate but not limit the invention.

EXAMPLE 1

A latex of ethyl acrylate (85 parts) and methacrylic acid (15 parts) was dissolved in 50 mole percent aqueous sodium hydroxide and then treated with 2 mole percent acetic acid to form an acidified polyelectrolyte solution which was 25% solids (pH about 6). Oxyethylene-bis-(2-oxazoline), (1.5% by weight of the polymer) was dissolved in the polyelectrolyte solution and a 25 mil film was drawn on a chrome plate. After air drying, the film was cured in a 150° oven for 16 hours. One gram of cured film was swollen in excess 0.27 N NaCl solution and filtered to give 51 grams of firm gel (absorbency 51 g/g).

EXAMPLES 2–12

An acrylic polyelectrolyte solution was prepared as in Example 1 except that 10 mole percent of acetic acid was used. Portions of this acidic polyelectrolyte solution were then mixed with various amounts of curing agents and cast as films on mirror-finish chrome sheet. After air drying, the films were stripped from the sheet and cured in an oven set at 150°C for the times indicated below. Cure times in excess of one hour have no further effect on the polymer but were done for convenience. Absorbency was measured in the usual way by swelling the tared film in excess 0.27 n NaCl solution, draining, and weighing gel.

The results are shown in Table I.

TABLE I

| Example | CURING AGENT Type | Wt. % of Polymer | Cure Time (hrs) | Absorbency (g 0.27 n NaCl/ g polymer) |
|---|---|---|---|---|
| 2 | 2,2'-bis-(2-oxazoline) | 0.2 | 17 | 68.4 |
| 3 | 2,2'-bis-(2-oxazoline) | 1.0 | 15.5 | 19.8 |
| 4 | 2,2'-bis-(2-oxazoline) | 5.0 | 7.5 | 11.8 |
| 5 | thiodiethylene-bis-(2-oxazoline) | 0.2 | 17 | 79.8 |
| 6 | thiodiethylene-bis-(2-oxazoline) | 1.0 | 15.5 | 19.8 |
| 7 | thiodiethylene-bis-(2-oxazoline) | 5.0 | 7.5 | 11.8 |
| 8 | tetramethylene-bis-(2-oxazoline) | 0.1 | 17 | 77 |
| 9 | tetramethylene-bis-(2-oxazoline) | 0.2 | 17 | 36.4 |
| 10 | tetramethylene-bis-(2-oxazoline) | 1.0 | 15.5 | 17.4 |
| 11 | tetramethylene-bis-(2-oxazoline) | 5.0 | 7.5 | 8.8 |
| 12 | oxydiethylene-bis-(2-oxazoline) | 0.2 | 17 | 54.4 |

This data illustrates the high reactivity of these crosslinking agents. It also shows that the polymer absorbency (swellability) drops substantially at higher levels of curing agent. The actual absorbency of choice depends on the particular end-use. Where the product is subjected to considerable physical abuse (as in a bath mat) a stronger, albeit less absorbent, polymer may be preferable to a highly swellable variety.

EXAMPLES 13–15

An 80/20 (by weight) copolymer of sodium styrene sulfonate and acrylic acid was prepared at 22.7% solids in water by heating the solution at 50°C. for 4 days. Calculated amounts of tetramethylene-bis-(2-oxazoline) curing agent were dissolved in polymer solution and films cast, dried and cured at 150°C. Gel capacity (absorbency) was determined as usual in 0.27 n NaCl solution. The results are shown in Table II.

TABLE II

| Example | Curing Agent Wt. % of Polymer | Cure Time (hrs) | Gel Capacity (g/g) |
|---|---|---|---|
| 13 | 5% | 7.5 | 9.4 |
| 14 | 1% | 15.5 | 14.4 |
| 15 | 0.2% | 17 | 42 |

EXAMPLES 16–18

A 75/25 (by moles) copolymer of sodium acrylate and acrylic acid prepared by adding the calculated amount of sodium hydroxide to a polyacrylic acid solution (Rohm and Haas Acrysol A-5). Films were case containing various amounts of tetramethylene-bis-(2-oxozoline) curing agent and worked up as described above. Results are shown in Table III.

TABLE III

| Example | Curing Agent Wt. % of Polymer | Cure Time (hrs) | Gel Capacity g/g |
|---|---|---|---|
| 16 | 5% | 7.5 | 9.4 |
| 17 | 1.0% | 15.5 | 19.6 |
| 18 | 0.2% | 17 | 28 |

Tables II and III show that this method of preparing absorbent polyelectrolyte is very general as far as the polyelectrolyte is concerned. The crosslinking reaction depends only on the polymer possessing free carboxylic acid pendent groups and is independent of the composition of the remainder of the polymer as long as the polymer is water soluble before curing.

I claim:

1. A solution useful to form water swellable articles of a carboxylic synthetic polyelectrolyte which comprises
   1. a solvent consisting of water, or a mixture thereof with lower alcohols,
   2. about 5 to about 60% by weight based on the amount of solvent of a carboxylic polyelectrolyte or mixtures thereof having free carboxylic acid groups, and
   3. 0.05 to 5.0% by weight based on the polyelectrolyte of a bis-oxazoline or bis-imino-oxazolidino crosslinking agent reactive with carboxylic acid groups.

2. The solution as set forth in claim 1 wherein said crosslinking agent is selected from compounds having the formulas

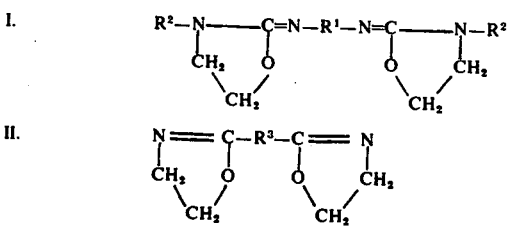

wherein $R_1$ is a divalent radical selected from alkylidenes, arylidenes, and cyclomethylidenes, $R_2$ is an alkyl group of one to ten carbons, cyclohexyl and phenyl, $R_3$ is selected from a single bond; oxydiethylene or oxydibutylene; thiodiethylene or thiodibutylene; or ethylene, or tetramethylene.

3. The solution as set forth in claim 1 wherein crosslinking agent is present in the amount from 0.2 to 0.5% by weight.

4. The solution as set forth in claim 1 wherein the solution has a pH in the range from 1.0 to 6.5.

5. The solution as set forth in claim 2 wherein said crosslinking agent has the formula

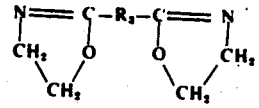

wherein $R_3$ is selected from a single bond; oxydiethylene or oxydibutylene; thiodiethylene or thiodibutylene; or ethylene, or tetramethylene.

6. The solution as set forth in claim 5 wherein the crosslinking agent is 2,2'-bis(2-oxazoline).

7. The solution as set forth in claim 5 wherein the crosslinking agent is thiodiethylene-bis-(2-oxazoline).

8. The solution as set forth in claim 5 wherein the crosslinking agent is tetramethylene-bis-(2-oxazoline).

9. The solution as set forth in claim 5 wherein the crosslinking agent is oxydiethylene-bis-(2-oxazoline).

10. A method of preparing a water swellable polyelectrolyte which comprises the steps of
    1. preparing a solution as set forth in claim 1,
    2. evaporating about 75% of the solvent therefrom to obtain a substantially dry water swellable crosslinked polyelectrolyte.

11. A method of preparing a swellable polyelectrolyte which comprises the steps of
    1. preparing a solution as set forth in claim 2,
    2. evaporating about 75% of the solvent therefrom to obtain a substantially dry water swellable crosslinked polyelectrolyte.

12. The substantially dry water swellable cross-linked polyelectrolyte produced by the method of claim 10.

13. The substantially dry water swellable cross-linked polyelectrolyte produced by the method of claim 11.

* * * * *